(12) United States Patent
Ode

(10) Patent No.: US 9,335,253 B2
(45) Date of Patent: May 10, 2016

(54) PHOTOACOUSTIC MICROSCOPE FOR DETECTING REFLECTED DETECTION LIGHT RESULTING FROM MODULATION BY SPECIMEN

(71) Applicant: OLYMPUS CORPORATION, Tokyo (JP)

(72) Inventor: Hisashi Ode, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 14/559,312

(22) Filed: Dec. 3, 2014

(65) Prior Publication Data

US 2015/0085296 A1 Mar. 26, 2015

Related U.S. Application Data

(63) Continuation of application No. PCT/JP2013/003862, filed on Jun. 20, 2013.

(30) Foreign Application Priority Data

Jun. 20, 2012 (JP) .................................. 2012-138981

(51) Int. Cl.
  *G01B 9/02* (2006.01)
  *G01N 21/17* (2006.01)
  (Continued)

(52) U.S. Cl.
  CPC ........ *G01N 21/1702* (2013.01); *G01B 9/02007* (2013.01); *G01B 9/02091* (2013.01); *G01B 21/02* (2013.01); *G01N 29/0672* (2013.01); *G01N 29/0681* (2013.01);
  (Continued)

(58) Field of Classification Search
  CPC ............. A61B 5/0062; G01B 2290/50; G01B 9/02091
  See application file for complete search history.

(56) References Cited

U.S. PATENT DOCUMENTS

| | | | | |
|---|---|---|---|---|
| 7,236,251 B2* | 6/2007 | Takaoka | | 356/497 |
| 8,896,842 B2* | 11/2014 | Bower et al. | | 356/497 |
| 2005/0213103 A1* | 9/2005 | Everett et al. | | 356/479 |

FOREIGN PATENT DOCUMENTS

| | | |
|---|---|---|
| JP | H07-159381 A | 6/1995 |
| JP | 2011-519281 A | 7/2011 |

OTHER PUBLICATIONS

Rousseau, Guy et al., "Non-contact photoacoustic tomography and ultrasonography for tissue imaging", Biomedical Optics Express (2012), vol. 3, No. 1, pp. 16-25.

(Continued)

*Primary Examiner* — Hwa Lee
(74) *Attorney, Agent, or Firm* — Scully, Scott, Murphy & Presser, P.C.

(57) ABSTRACT

Provided is a photoacoustic microscope, including: an objective lens configured to collect excitation light into a specimen, the excitation light in a wavelength range that is absorbed by an object to be observed; a detection light optical system configured to (i) form an image of a point light source of detection light in a middle portion of a pupil of the objective lens, the detection light having a wavelength that is different from the wavelength range of the excitation light, and (ii) emit the detection light onto the specimen by means of the objective lens; an optical scanning unit configured to deflect the excitation light and the detection light that enter the objective lens, for scanning the specimen; and a light detection unit configured to detect reflected light of the detection light that is reflected by the specimen.

4 Claims, 3 Drawing Sheets

(51) Int. Cl.
*G01N 29/06* (2006.01)
*G01N 29/24* (2006.01)
*G02B 21/00* (2006.01)
*G01B 21/02* (2006.01)

(52) U.S. Cl.
CPC ......... *G01N 29/2418* (2013.01); *G02B 21/002* (2013.01); *G01N 2021/1706* (2013.01); *G01N 2201/0697* (2013.01); *G01N 2201/06113* (2013.01); *G01N 2201/08* (2013.01); *G01N 2201/10* (2013.01); *G01N 2201/125* (2013.01)

(56) References Cited

OTHER PUBLICATIONS

Wang, Yi et al., "Noncontact photoacoustic imaging achieved by using a low-coherence interferometer as the acoustic detector", Optics Letters (Oct. 15, 2011), vol. 36, No. 20, pp. 3975-3977.
International Search Report dated Sep. 24, 2013 issued in PCT/JP2013/003862.

\* cited by examiner

PHOTOACOUSTIC MICROSCOPE FOR DETECTING REFLECTED DETECTION LIGHT RESULTING FROM MODULATION BY SPECIMEN

CROSS-REFERENCE TO RELATED APPLICATION

The present application is a Continuing Application based on International Application PCT/JP2013/003862 filed on Jun. 20, 2013, which, in turn, claims the priority from Japanese Patent Application No. 2012-138981 filed on Jun. 20, 2012, the entire contents of which are incorporated herein by reference.

TECHNICAL FIELD

The present invention relates to a photoacoustic microscope.

BACKGROUND

Photoacoustic wave is a kind of elastic wave that is generated in a thermoelastic process occurring when light in a wavelength range that is to be absorbed by the material is emitted to the material, and therefore, photoacoustic wave has attracted attention as a method for imaging absorption properties. Photoacoustic wave is also a kind of ultrasonic wave and characterized by low susceptibility to scattering compared with light. Accordingly, photoacoustic wave is employed as a method for in vivo imaging.

Photoacoustic microscopes that employ photoacoustic waves as detection signals for the purpose of imaging use, as excitation light, pulsed light corresponding to a wavelength range that is absorbed by an object to be observed. Such a photoacoustic microscope uses a technique of scanning in a specimen by a spot focused by an objective lens and detecting photoacoustic waves generated in different spots by means of a transducer or the like. According to the photoacoustic microscope, since, during the scanning in the specimen by a spot, the presence of an absorbing material in a focal point of the light generates a photoacoustic wave, the absorption properties in the specimen are imaged by detecting the generated photoacoustic wave.

Examples of such a photoacoustic microscope which are known include the one that is designed to improve spatial resolution. (Refer to, for example, Patent Literature 1.) In the above photoacoustic microscope, as FIG. 3 schematically illustrates a part thereof, excitation light L emitted from a laser pulse light source (which is not illustrated) passes through a condenser lens 101, a pin hole 102, an objective lens 103, a correcting lens 104, a triangular prism 105, silicon oil 106, a triangular prism 107, and an ultrasonic lens 108, and then, the excitation light L is focused into the specimen S. The triangular prisms 105 and 107 are coupled via the silicon oil 106. The specimen S is immersed in a liquid 110 in a liquid immersion bath 109. A photoacoustic wave U generated by the specimen S is collected by the ultrasonic lens 108 and enters the triangular prism 107, and then, reflected by an interface of the triangular prism 107 and the silicon oil 106 and detected by an ultrasonic transducer 111.

That is to say, in the photoacoustic microscope illustrated in FIG. 3, an excitation optical system and an ultrasonic wave guide system are coaxially arranged with use of the triangular prisms 105 and 107, and moreover, the objective lens 103 for focusing the light and the ultrasonic lens 108 for detecting an ultrasonic wave are arranged in a manner such that focal points thereof have a conjugate relation, so that the focused spot of the excitation light and the spot for detection of the ultrasonic wave are focused onto the same spot. With the above configuration, when, for example, a laser pulse light having a wavelength of 630 nm is used as the excitation light, an objective lens having a numerical aperture (NA) of 0.1 is used as the objective lens 103, and the excitation light is focused onto the specimen S with a diffraction limit of approximately 3.8 μm, an approximately 5-μm lateral resolution of photoacoustic wave is achieved.

However, since the photoacoustic microscope configured as illustrated in FIG. 3 detects a photoacoustic wave U with use of the ultrasonic transducer 111, when air is present in a wave guide for the photoacoustic wave U located between the specimen S and the ultrasonic transducer 111, the photoacoustic wave U is prevented from propagation. For the above reason, in the photoacoustic microscope illustrated in FIG. 3, it is required to immerse the specimen S and the ultrasonic lens 108 in the liquid 110 and to fill a liquid such as water and oil between adjacent elements disposed in the wave guide. The above requirements might result in limitation to the specimen S and a complicated configuration of a signal detection system.

On the other hand, the examples of the photoacoustic microscope also include the one that is capable of non-contact detection of a photoacoustic wave by utilizing vibration of a surface of a specimen that is caused when the photoacoustic wave generated inside the specimen in response to emission of excitation light propagates to the surface of the specimen. In the above photoacoustic microscope, a liquid such as oil is poured on the surface of the specimen or into the specimen, and detection light, which is different from excitation light, is focused onto a surface of the liquid so as to detect the detection light being modulated by the vibration of the surface of the specimen. As a method for the detection of modulated light, the Optical Coherence Tomography (OCT) (as described in Non-Patent Literature 1) and the light heterodyne method (as described in Non-Patent Literature 2) are known. Since the above photoacoustic microscope does not detect a photoacoustic wave directly but detects a photoacoustic wave by converting the photoacoustic wave into modulated light, the limitation to the specimen is significantly reduced, and the signal detection system may be configured in a simple manner.

CITATION LIST

Patent Literature

Patent Literature 1: Japanese Translation of PCT International Application Publication No. 2011-519281

Non-Patent Literatures

Non-Patent Literature 1: Guy Rousseau, Alain Blouin, and Jean-Pierre Monchalin, *Non-Contactphotoacoustic Tomography and Ultrasonography for Tissue Imaging*, in Biomed Opt. Express, Vol. 3 Issue 1, p. 16 (2012)

Non-Patent Literature 2: Yi Wang, Chunhui Li, and Ruikang K. Wang, *Noncontactphotoacoustic Imaging Achieved by Using a Low-Coherence Interferometer as the Acoustic Detector*, in Opt. Lett., Vol. 36 Issue 20, p. 3975 (2011)

SUMMARY OF INVENTION

One aspect of the present invention resides in a photoacoustic microscope, including: an objective lens configured to collect excitation light into a specimen, the excitation light being in a wavelength range that is absorbed by an object to be observed; a detection light optical system configured to (i) form an image of a point light source of detection light in a middle portion of a pupil of the objective lens, the detection light having a wavelength that is different from the wavelength range of the excitation light, and (ii) emit the detection light onto the specimen by means of the objective lens; an optical scanning unit configured to deflect the excitation light and the detection light that enter the objective lens, for scanning the specimen; and a light detection unit configured to detect reflected light of the detection light that is reflected by the specimen.

In one embodiment according to the above aspect of the present invention, the light detection unit detects the reflected light by the optical coherence tomography.

In another embodiment according to the above aspect of the present invention, the light detection unit detects the reflected light by the light heterodyne method.

BRIEF DESCRIPTION OF DRAWINGS

The present invention will be further described below with reference to the accompanying drawings, wherein.

DESCRIPTION OF EMBODIMENTS

Embodiments of the present invention will be described below with reference to the drawings.

First Embodiment

Figure 1:
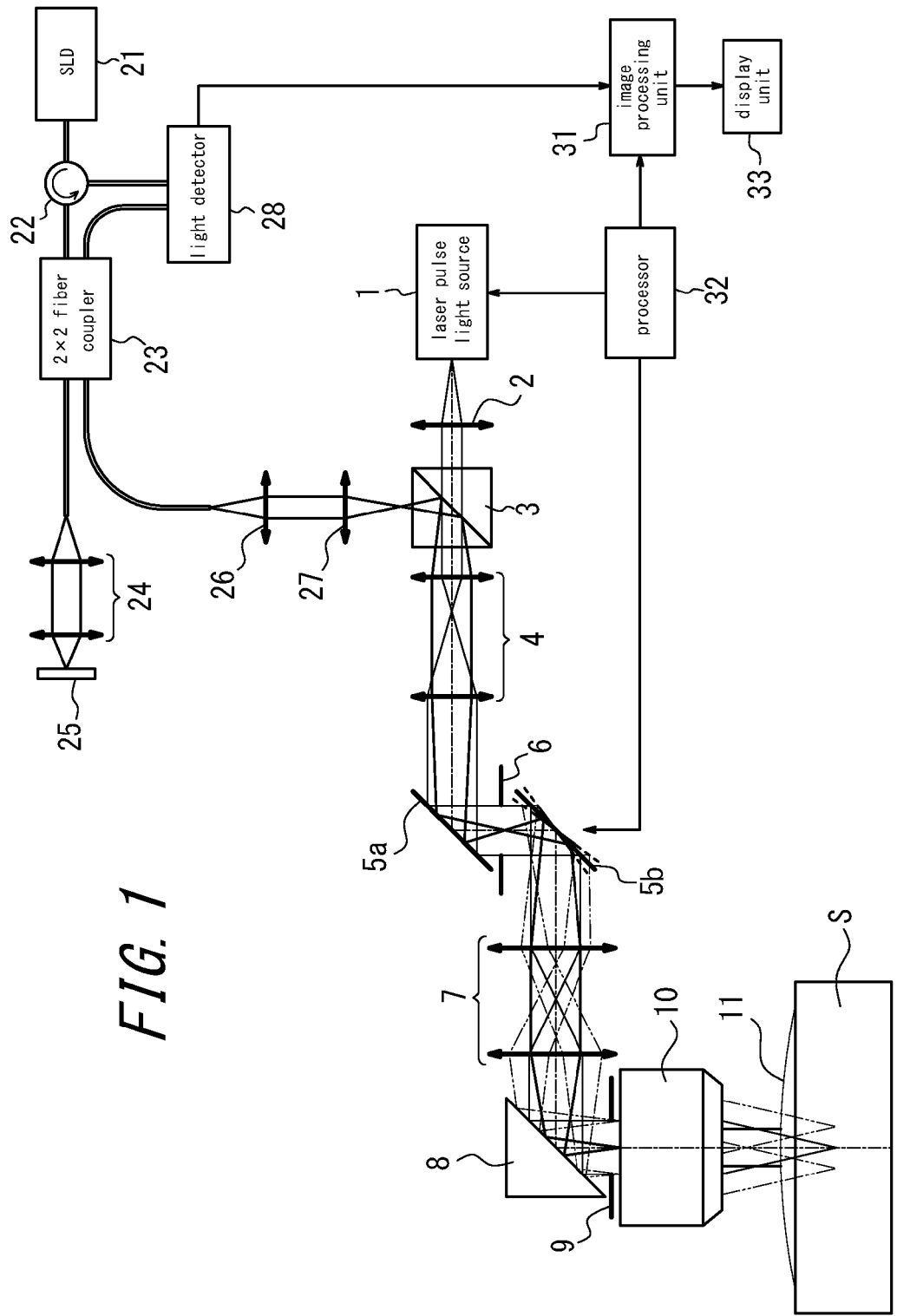
FIG. 1 schematically illustrates a configuration of a part of a photoacoustic microscope according to the first embodiment.

FIG. 1 schematically illustrates a configuration of a part of a photoacoustic microscope according to the first embodiment of the present invention. The photoacoustic microscope according to the present embodiment uses, as excitation light, pulsed light emitted from a laser pulse light source 1. As the excitation light, for example in a case of imaging of a blood vessel of the specimen S which is a living body, light in a wavelength range that is absorbed by hemoglobin is used. It should be noted that the object to be observed is not limited to a blood vessel, and as the excitation light, any light in a wavelength range corresponding to the object to be observed may be used. In a case where a plurality of absorbing objects is present in the specimen S, it is preferable to use light having a peak wavelength of an absorption spectrum that is characteristic of the objects to be observed. The excitation light from the laser pulse light source 1 is emitted from a collimator lens 2 as parallel light.

As the detection light, light having a wavelength (e.g. a continuous wave) that is different from the wavelength range of the excitation light is used. The detection light is emitted from a SLD (Super Luminescent Diode) 21, which is a low coherence light source. In the photoacoustic microscope according to the present embodiment, the Optical Coherence Tomography (OCT) is employed in order to detect a reflected light of the detection light (which may be referred to below as a reflected detection light) that is modulated by a photoacoustic wave generated by the specimen S in response to emission of the excitation light.

In FIG. 1, after emitted as the parallel light from the collimator lens 2, the excitation light (the pulsed light) passes through a beam splitter 3, a first relay optical system 4, a galvanometer mirror 5a, a first pupil (an aperture stop) 6, a galvanometer mirror 5b, a second relay optical system 7, a reflecting mirror 8, and a second pupil (an aperture stop) 9. Then, by means of an objective lens 10, the excitation light is focused into the specimen S through a liquid droplet 11. The galvanometer mirrors 5a and 5b herein constitute an optical scanning unit. By the galvanometer mirrors 5a and 5b, the light emitted to the specimen S is two-dimensionally scanned in a plane orthogonal to an optical axis of the objective lens 10. In FIG. 1, for simplification of the figure, the galvanometer mirrors 5a and 5b are illustrated as swingable in the same plane. The second pupil 9 is disposed in a posterior focal point of the objective lens 10, and the first pupil 6 is arranged in the middle of an optical path of the galvanometer mirrors 5a and 5b in a manner such that the first pupil 6 is placed in a conjugate position with the second pupil 9.

On the other hand, light emitted from the SLD 21 passes through a circulator 22 and then is split into reference light and detection light by a 2×2 fiber coupler 23. The reference light resulting from the split by the 2×2 fiber coupler 23 passes through a reference light optical system 24 and then is reflected by a reflecting mirror 25. After that, the reference light passes through the reference light optical system 24 again and then enters the 2×2 fiber coupler 23.

The detection light resulting from the split by the 2×2 fiber coupler 23 is converted by the collimator lens 26 into parallel light. Subsequently, the detection light passes through a condenser lens 27, which constitutes a detection light optical system, and then enters the beam splitter 3 to be synthesized coaxially with the excitation light. After that, the detection light passes through the first relay optical system 4, the galvanometer mirror 5a, the first pupil 6, the galvanometer mirror 5b, the second relay optical system 7, the reflecting mirror 8, and the second pupil 9, all of which constitute the mutual optical system of the excitation light and the detection light. Then, by means of the objective lens 10, the detection light is emitted to the specimen S.

The condenser lens 27 is positioned in a manner such that an image of a point light source of the detection light is formed in middle portions of the first pupil 6 and the second pupil 9 of the objective lens 10. With the above configuration, the objective lens 10 emits, as a telecentric optical system, the detection light in the form of substantially parallel light to the specimen S. Accordingly, by swinging the galvanometer mirrors 5a and 5b and deflecting the excitation light and the detection light, the specimen S is two-dimensionally scanned coaxially by the excitation light and the detection light. As a result, the detection light is emitted to an area of the specimen S in which a photoacoustic wave generated in response to the excitation light easily propagates.

When the excitation light is focused into the specimen S, depending on the presence of the object to be observed, a photoacoustic wave is generated, resulting in the vibration of the surface of the specimen S. By the vibration of the surface of the specimen S, the detection light, which has been emitted simultaneously with the excitation light, is modulated and reflected. The reflected detection light resulting from the modulation by the specimen S travels along a path that is reverse to the outgoing path to enter the 2×2 fiber coupler 23 for the detection by the OCT. That is to say, the reflected detection light is interfered with by the reference light in the 2×2 fiber coupler 23, and the interfered light is received by a light detector 28 directly or via the circulator 22. With the above configuration, the displacement of the surface of the specimen S is detected as a change in interference signal strength. Thus, the circulator 22, the 2×2 fiber coupler 23, the reference light optical system 24, the reflecting mirror 25, and the light detector 28 constitute a light detection unit.

An output from the light detector 28 is supplied to an image processing unit 31. The laser pulse light source 1, the galvanometer mirrors 5a and 5b, and the image processing unit 31 are controlled in synchronization by a processor 32. With the above configuration, image data based on a photoacoustic wave is generated in the image processing unit 31, and the generated image data is displayed on a display unit 33.

According to the photoacoustic microscope of the present embodiment, by deflecting the excitation light by means of the galvanometer mirrors 5a and 5b, the specimen S is scanned by simultaneously deflecting the detection light in the form of the parallel light, while the optical axis of the excitation light substantially corresponds to the optical axis of the detection light. Accordingly, the photoacoustic microscope of the present embodiment makes it possible to effectively detect the reflected detection light resulting from the modulation due to the vibration of the surface of the specimen S caused when a photoacoustic wave generated in response to emission of the excitation light propagates to the surface of the specimen S. Furthermore, since the excitation light and the detection light are scanned by the galvanometer mirrors 5a and 5b, rapid scanning is achieved, and the specimen S does not suffer from the vibration found in the case of stage scanning. Accordingly, the reflected detection light resulting from the modulation by the specimen S is detected reliably with high precision, and an image with a high S/N ratio is acquired within a short period of time.

When the depth of observation of the specimen S is desired to be altered, the focal point of the excitation light may be altered by displacing the objective lens 10 and/or the stage (which is not illustrated) on which the specimen S is located in a direction of the optical axis of the objective lens 10. Then, by deflecting the excitation light and the detection light by means of the galvanometer mirrors 5a and 5b with use of the altered focal point of the light and by two-dimensionally scanning the specimen S in the plane orthogonal to the optical axis of the objective lens 10, an image of a different depth is quickly acquired.

In the above regard, when the focal point of the light is altered by displacing the objective lens 10 in the direction of the optical axis, the position of the second pupil 9 of the objective lens 10 is also displaced in the direction of the optical axis. Accordingly, in the above circumstance, in conjunction with the displacement of the objective lens 10, the condenser lens 27 needs to be displaced in the direction of the optical axis. However, in the above circumstance, there is no need to focus the detection light onto the surface of the liquid droplet 11 poured on the specimen S, and it is only necessary to form the image of the point light source of the detection light in the middle portion of the displaced second pupil 9 so that the detection light is emitted from the objective lens 10 in the form of substantially parallel light. Accordingly, the condenser lens 27 is adjusted easily. With the above configuration, even after the displacement of the objective lens 10, the detection light may be emitted to the specimen S in the form of substantially parallel light in a manner such that the detection light is coaxial with the excitation light, that is to say, over a principal ray of the excitation light. Thus, the photoacoustic microscope of the present embodiment is capable of easily coping with the case where the depth of observation is desired to be altered by displacing the objective lens 10, making it possible to detect the displacement of the specimen S reliably with high precision at a desired depth of observation.

Moreover, according to the photoacoustic microscope of the present embodiment, since the reflected detection light resulting from the modulation by the specimen S is detected by the OCT, which is interference measurement using the SLD 21, namely, the low coherence light source, it is possible to selectively detect a signal reflected by a specific reflecting surface. Even when a light component reflected by an interface located inside the specimen S is present, only a light component reflected by the surface of the specimen S may be detected. Accordingly, the reflected detection light is detected with high sensitivity.

As illustrated in FIG. 1, it is preferable to form the liquid droplet 11 on the surface of the specimen S. The reason is that, when the specimen S has, for example, a coarse, a locally uneven, or a ramped surface, due to an influence of scattering, the reflected detection light to be detected is deteriorated, and the strength of the reflected detection light varies each time the reflected detection light is detected in a different scanning position, which lead to difficulty in detection of a reliable signal. In contrast, with the liquid droplet 11 formed on the surface of the specimen S, a smooth and substantially flat surface of the liquid droplet 11 is provided regardless of a shape of the surface of the specimen S. Furthermore, since the liquid droplet 11 propagates photoacoustic waves, the surface vibration caused by a photoacoustic wave propagated to the surface of the specimen S also propagates through the liquid droplet 11, resulting in the vibration of the surface of the liquid droplet 11. Accordingly, by detecting the reflected detection light on the surface of the liquid droplet 11, a modulation component of the detection light is detected. At this time, on the surface of the liquid droplet 11, it is possible to suppress the influence of surface scattering, and therefore, reliable detection is achieved. The material of the liquid droplet 11 is not limited to water, and any liquid, gel, or the like that propagates photoacoustic waves and that forms a smooth surface may also be used.

Additionally, by adjusting the numerical aperture of the detection light whose image is formed at positions where the pupils of the object lens 10 are located, a luminous flux diameter of the parallel light of the detection light that is emitted from the objective lens 10 may be adjusted. For example, a larger numerical aperture will yield a larger luminous flux diameter of the parallel light emitted from the objective lens 10, and a smaller numerical aperture will yield a smaller luminous flux diameter. Accordingly, for example in accordance with the shape of the detected surface of the specimen S, the luminous flux diameter of the detection light may be easily optimized.

Second Embodiment

Figure 2:
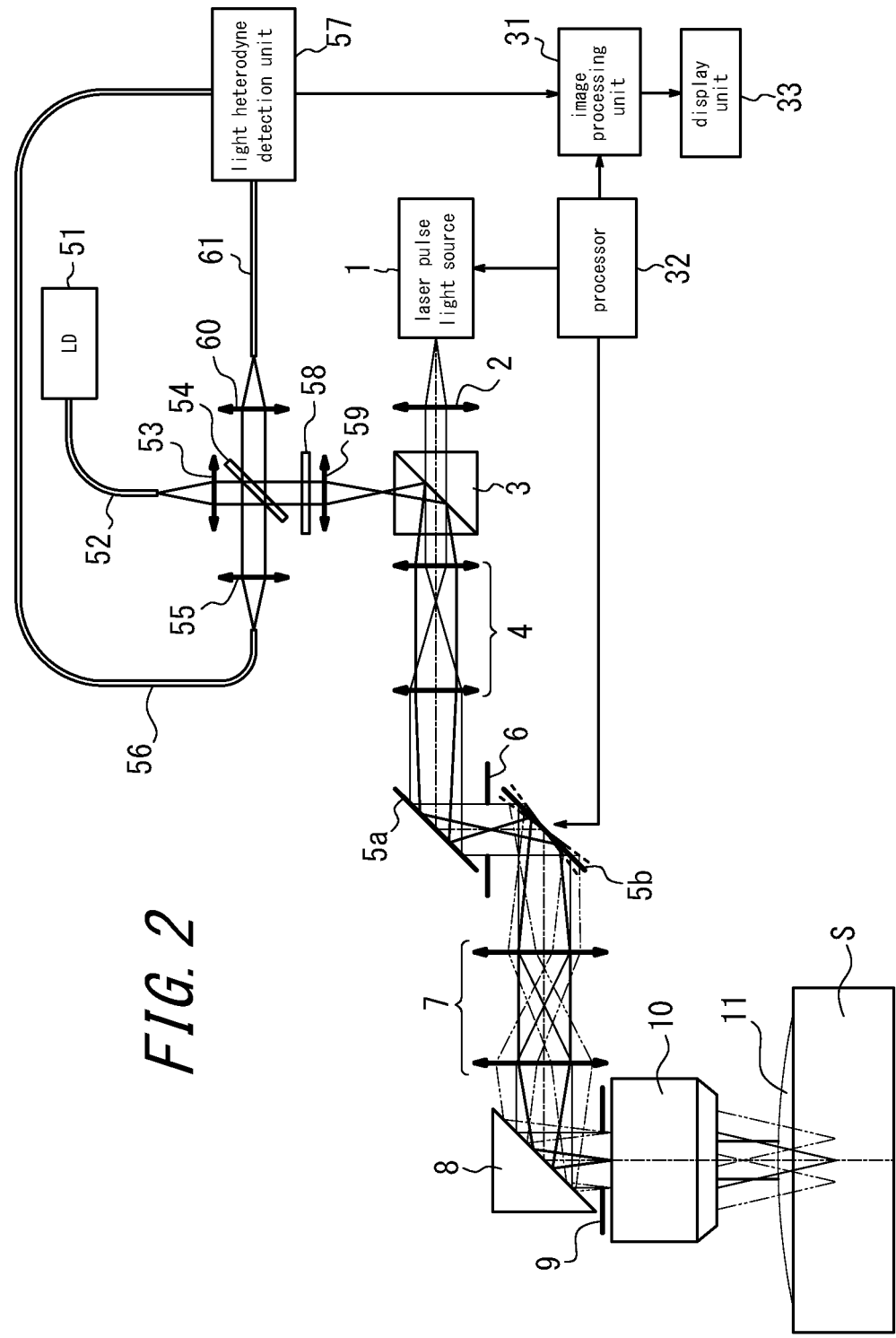
FIG. 2 schematically illustrates a configuration of a part of a photoacoustic microscope according to the second embodiment.
Figure 3:
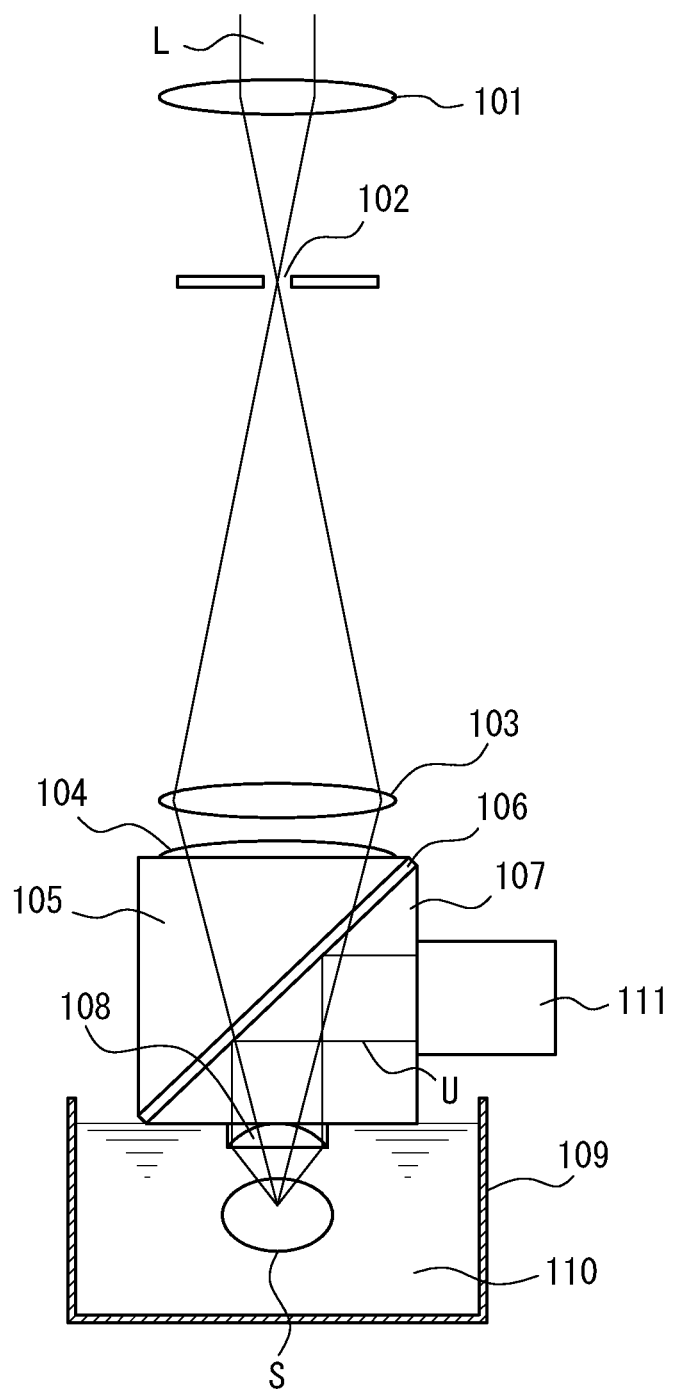
FIG. 3 schematically illustrates a configuration of a part of a conventional photoacoustic microscope.

FIG. 2 schematically illustrates a configuration of a part of a photoacoustic microscope according to the second embodiment of the present invention. The photoacoustic microscope according to the present embodiment differs from the photoacoustic microscope according to the first embodiment in terms of the configuration of the light detection unit. In details, although in the first embodiment the reflected detection light resulting from the modulation by the specimen S is detected by the OCT, in the present embodiment the reflected detection light resulting from the modulation by the specimen S is detected by the light heterodyne method. Other configurations of the present embodiment are the same as those of the first embodiment. Accordingly, components with substantially the same functions as in FIG. 1 are denoted by the same reference numerals, and a description thereof is omitted.

The photoacoustic microscope according to the present embodiment uses, as the detection light, light having a wavelength (e.g. a continuous wave) that is different from the wavelength range of the excitation light. The detection light is emitted from a LD (Laser Diode) 51. Light emitted from the LD 51 passes through a fiber 52 and enters a collimator lens 53 to be converted into parallel light. Subsequently, the light is polarized and split by a polarizing beam splitter 54 into reference light and detection light which are linearly polarized beams of light with orthogonal polarizations. The reference light resulting from the split by the polarizing beam splitter 54 is collected by a condenser lens 55, and then passes through a fiber 56 and enters a light heterodyne detection unit 57.

On the other hand, the linearly polarized detection light resulting from the split by the polarizing beam splitter 54 is converted into circularly polarized light by a ¼ wavelength plate 58. Subsequently, the detection light passes through a condenser lens 59, which constitutes the detection light optical system, and then enters the beam splitter 3 to be synthesized coaxially with the excitation light. Similarly to the first embodiment, the detection light passes through the first relay optical system 4, the galvanometer mirror 5a, the first pupil 6, the galvanometer mirror 5b, the second relay optical system 7, the reflecting mirror 8, and the second pupil 9, all of which constitute the mutual optical system of the excitation light and the detection light. Then, by means of the objective lens 10, the detection light is emitted to the specimen S. The condenser lens 59 is positioned in a manner such that an image of a point light source of the detection light is formed in the middle portions of the first pupil 6 and the second pupil 9 of the objective lens 10, in accordance with a position of the objective lens 10 on the optical axis.

The reflected detection light resulting from the modulation by the specimen S is emitted from the beam splitter 3 and travels along a path that is reverse to the outgoing path to pass through the condenser lens 59 and enter the ¼ wavelength plate 58. By transmitted through the ¼ wavelength plate 58, the reflected detection light is converted into linearly polarized light that is orthogonal to the detection light in the outgoing path in polarization direction and then reflected by the polarizing beam splitter 54. After reflected by the polarizing beam splitter 54, the reflected detection light is collected by a condenser lens 60 and then passes through a fiber 61 to enter the light heterodyne detection unit 57.

The light heterodyne detection unit 57 is configured to measure light heterodyne interference between the incident reference light and reflected detection light and to detect a frequency modulation component caused by the displacement of the surface of the specimen S as a change in interference signal strength. Thus, in the present embodiment, the polarizing beam splitter 54, the condenser lens 55, the fiber 56, the light heterodyne detection unit 57, the ¼ wavelength plate 58, the condenser lens 60, and the fiber 61 constitute the light detection unit.

Similarly to the first embodiment, an output from the light heterodyne detection unit 57 is supplied to the image processing unit 31. The laser pulse light source 1, the galvanometer mirrors 5a and 5b, and the image processing unit 31 are controlled in synchronization by the processor 32. With the above configuration, image data based on a photoacoustic wave is generated in the image processing unit 31, and the generated image data is displayed on the display unit 33.

In the photoacoustic microscope according to the present embodiment also, the advantageous effects similar to those according to the first embodiment are achieved. For example, in the present embodiment, since the reflected detection light resulting from the modulation by the specimen S is detected by the light heterodyne method, by mixing the detection light prior to the modulation and the reflected detection light as a result of the modulation in the light heterodyne detection unit 57, a slight difference in frequency is detected. Accordingly, the reflected detection light from the specimen S is detected with even higher sensitivity.

The present invention is not strictly limited to the above embodiments, and various changes and modifications may be made to the embodiments. For example, the excitation light may be introduced from the laser pulse light source 1 to the collimator lens 2 through a fiber.

REFERENCE SIGNS 1 laser pulse light source
2 collimator lens
3 beam splitter
4, 7 relay optical system
5a, 5b galvanometer mirror
6, 9 pupil (aperture stop)
8 reflecting mirror
10 objective lens
11 liquid droplet
21 SLD
22 circulator
23 2×2 fiber coupler
24 reference light optical system
25 reflecting mirror
26 collimator lens
28 light detector
31 image processing unit
32 processor
33 display unit
51 LD
52, 56, 61 fiber
53 collimator lens
54 polarizing beam splitter
55 condenser lens
57 light heterodyne detection unit
58 ¼ wavelength plate
59, 60 condenser lens
S specimen

The invention claimed is:
1. A photoacoustic microscope, comprising:
an excitation light source configured to emit excitation light, wherein the excitation light is in a wavelength range that is absorbed by an object to be observed;
a detection light source configured to emit detection light, wherein the detection light has a wavelength that is different from the wavelength range of the excitation light;
an objective lens configured to collect the excitation light into a specimen;
a beam combiner configured to synthesize the detection light coaxially with the excitation light;
a condenser lens arranged between the detection light source and the beam combiner, wherein the condenser lens is arranged at a position that forms a point image of the detection light source in a middle portion of a pupil of the objective lens, so that the detection light is emitted onto the specimen by means of the objective lens;
an optical scanning unit arranged between the beam combiner and the objective lens, wherein the optical scan- ning unit is configured to deflect the excitation light and the detection light that enter the objective lens, for scanning the specimen; and a light detection unit configured to detect reflected light of the detection light that is reflected by the specimen.

2. The photoacoustic microscope of claim 1, wherein the light detection unit comprises:

a beam splitter configured to split light emitted from the detection light source into reference light and the detection light; and a reflecting mirror configured to reflect the reference light; and a light detector configured to detect interfered lights between the reflected light of the detection light that is reflected by the specimen and the reference light reflected by the reflecting mirror, wherein the light detection unit is configured to detect displacement of a surface of the specimen by optical coherence tomography.

3. The photoacoustic microscope of claim 1, wherein the light detection unit comprises:

a beam splitter configured to split light emitted from the detection light source into reference light and the detection light; and a light detector configured to measure heterodyne interference between the reference light and reflected light of the detection light that is reflected by the specimen, wherein the light detection unit is configured to detect displacement of a surface of the specimen by a light heterodyne method.

4. The photoacoustic microscope of claim 1, wherein the light detection unit comprises:

a polarization beam splitter configured to split light emitted from the detection light source into reference light and the detection light, which are linearly polarized beams of light with orthogonal polarizations;

a ¼ wavelength plate configured to convert the detection light from the polarization beam splitter into circularly polarized light and to convert the reflected light of the detection light that is reflected by the specimen into linearly polarized light; and a light detector configured to measure heterodyne interference between the reference light and the reflected light of the detection light converted into the linearly polarized light by the ¼ wavelength plate, wherein the light detection unit is configured to detect displacement of a surface of the specimen by a light heterodyne method.

\* \* \* \* \*